United States Patent [19]
Koros et al.

[11] Patent Number: 5,893,831
[45] Date of Patent: Apr. 13, 1999

[54] RETRACTOR BLADE LOCKING MECHANISM

[76] Inventors: Tibor B. Koros; Gabriel J. Koros, both of 610 Flinn Ave., Moorpark, Calif. 93021

[21] Appl. No.: 09/045,773

[22] Filed: Mar. 19, 1998

[51] Int. Cl.⁶ .................................................. A61B 17/02
[52] U.S. Cl. ........................ 600/232; 600/215; 600/222
[58] Field of Search ............................. 600/201, 215, 600/222, 232, 231, 230, 233; D24/228, 135

[56] References Cited

U.S. PATENT DOCUMENTS

| | | | |
|---|---|---|---|
| D. 361,381 | 8/1995 | Koros et al. | D24/135 |
| 4,213,451 | 7/1980 | Swenson | 600/215 |
| 5,052,373 | 10/1991 | Michalson | 600/232 |
| 5,067,477 | 11/1991 | Santangelo | 600/222 |
| 5,231,974 | 8/1993 | Giglio et al. | 600/215 |
| 5,616,117 | 4/1997 | Dinkler et al. | 600/222 |
| 5,667,481 | 9/1997 | Villalta et al. | 600/231 |
| 5,795,291 | 8/1998 | Koros et al. | 600/232 |

*Primary Examiner*—Paul J. Hirsch
*Attorney, Agent, or Firm*—David O'Reilly

[57] ABSTRACT

An improved retractor blade mounting system for use in surgical instrument retractors. In one embodiment the system includes a mounting clip attached to a retractor blade that engages a longitudinal groove in the retractor arm. To assure a positive tight grip on retractor arm the clip has a tongue that fits a longitudinal groove in a retractor arm and has tapered or angled surface that abuts a sharp edge of the longitudinal groove preventing the blade from moving once installed. In an optional embodiment the mounting clip is provided with a narrower tongue that is constructed with a beveled surface that fits over the corner or edge of the longitudinal groove securely holding the clip on the retractor arm.

3 Claims, 2 Drawing Sheets

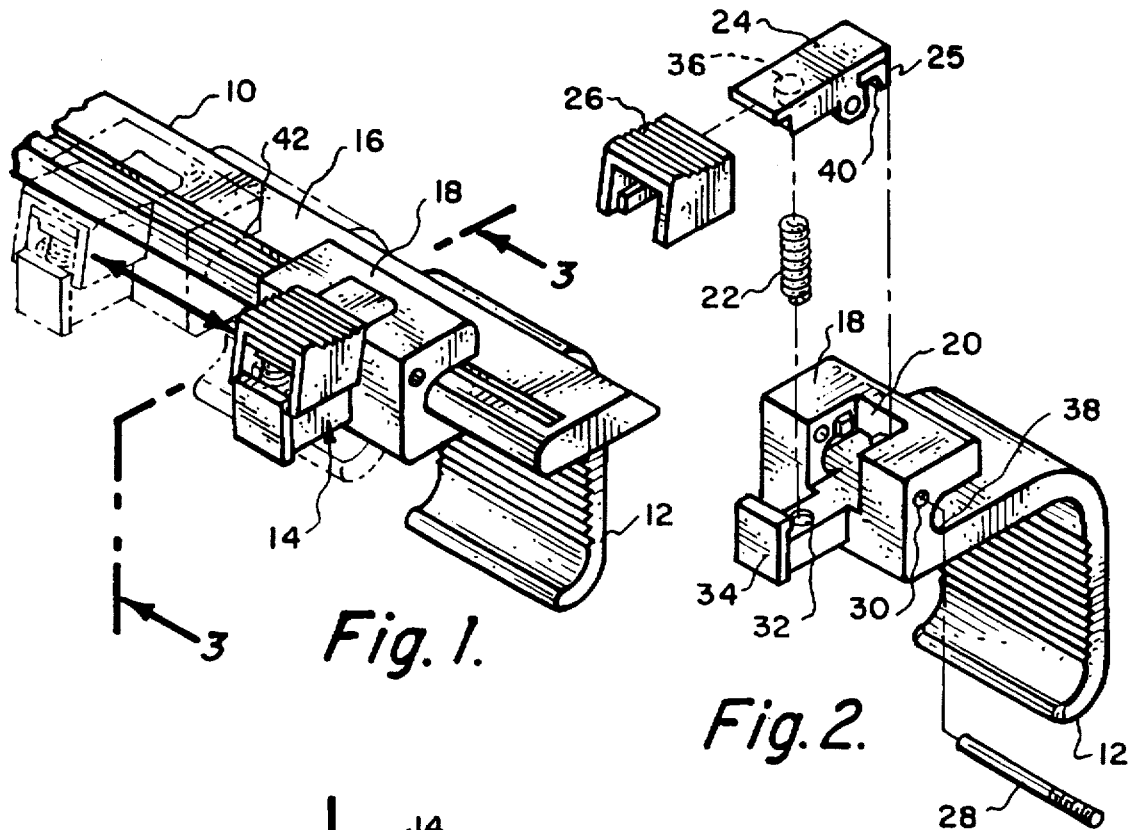
Fig. 1.
Fig. 2.
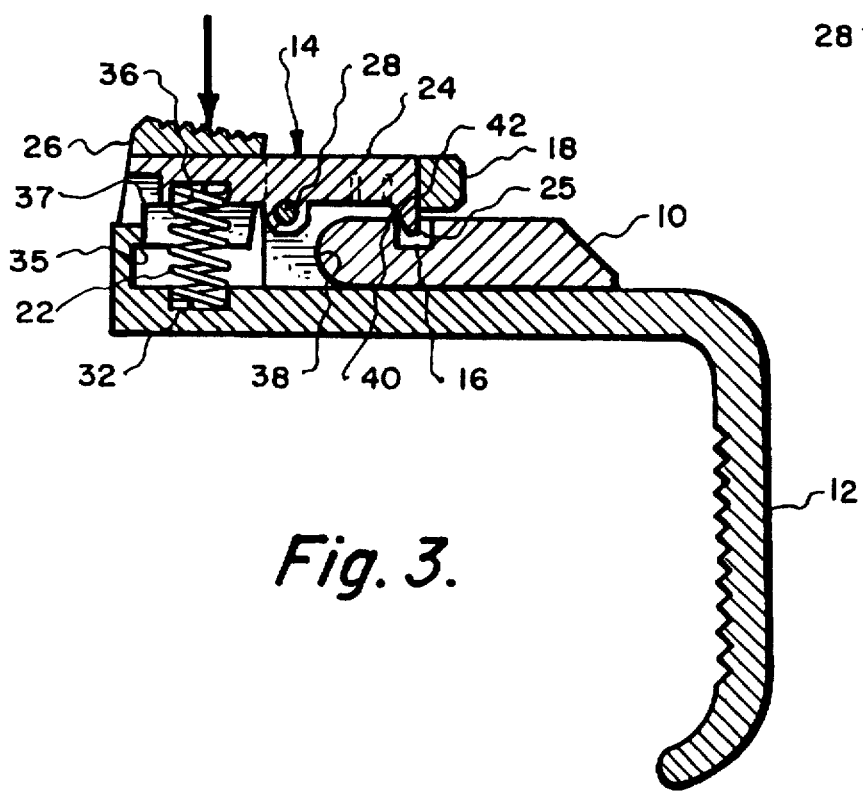
Fig. 3.

RETRACTOR BLADE LOCKING MECHANISM

BACKGROUND OF THE INVENTION

1. Field of the Invention

This invention relates to surgical instruments more particularly relates to an improved blade locking mechanism for retractors.

2. Background Information

Retractors are used to hold an incision open when performing surgical procedures. A variety of retractors are used for example to perform heart bypass operations or operations such as laminectomies.

A retractor is generally comprised of a pair of arms parallel to each extending from a cross bar. One of the arms is preferably fixed on the end of the cross bar while the other is mounted for movement by a crank and gear mechanism along cross bar. The retractor is placed in an incision with the arms nearly closed and the movable arm cranked open to spread and hold an incision open during surgery. One such surgical retractor is shown and described in U.S. Pat. No. Design 361,381 issued to the same inventors as the device disclosed herein.

After placement of these retractors, retractors blades are attached and positioned in the incision to hold tissue away from the surgical site. The retractor blades are generally adjustably mounted on the retractor arms. Preferably the retractor blades are mounted by a clip in a groove or channel in the retractor arms for adjustable movement parallel to the arms. The construction and arrangement of the arm and the groove allow for multiple blades to be mounted or removed to keep the surgical site clear of surrounding tissue.

A problem with present retractors is that the blades once positioned should remain fixed at the adjusted positions. However, due to the necessity of being able to slide the mounting clip holding the blade along the retractor arm, a tongue on the clip that fits into groove must move freely. The clip is generally spring loaded so that it securely clamps and holds the tongue on the clip in the groove at the adjusted position.

However, because the tongue is smaller than the groove the adjusted position is not as secure as desired. Since the tongue is smaller than the groove it can accidentally move and possibly interfere with the surgery. Therefore, it would be advantageous if an improved clip could be provided to substantially prevent movement of the blades once they are placed, adjusted, and securely positioned to hold tissue away from the surgical site.

It is, therefore, one object of the present invention to provide an improved locking mechanism to securely hold retractor blades in position once they are placed.

Another object of the present invention is to provide an improved blade mounting clip that securely holds a blade in position once the clip is positioned and released in the groove.

Still another object of the present invention is to provide an improved clip having the tongue with a beveled edge which when released engages an edge of the groove substantially preventing the clip and the adjusted position of the blade from changing.

Yet another object of the present invention is to provide an improved blade mounting clip having a tongue shaped to securely hold a blade in position in a substantially square cornered groove.

BRIEF DESCRIPTION OF THE INVENTION

The purpose of the present invention is to provide an improved blade mounting clip that securely holds blades in position on the arms of a retractor once the clip is released. This patent is related to surgical retractors such as that shown and described in U.S. Pat. No. Design 361,381 issued to the same inventors as the device herein and incorporated herein by reference.

Retractors for use when performing surgical procedure such as laminectomies, heart bypass operations and the like are comprised of a frame having a cross bar and a pair of rigid parallel arms extending perpendicular to the cross bar. One of the arms is preferably permanently attached to the end of the cross bar while the other arm is adjustable by a precision crank adjustment and a gear mechanism. A variety of detachable blades in various sizes are available for attachment to the arms. These retractors are used by placing them over an incision and attaching blades that extend into the body cavity to retract tissue around a surgical site to provide a clear view. Generally the blades are positioned and attached to the retractor arms by clamping them at various locations on the arms. Preferably they can be adjustably mounted on the arms for proper positioning in an incision.

The blades are generally attached to the arms by a clip that has a tongue engaging a longitudinal groove in the arm so that the blades can be adjusted horizontally anywhere along the arm. Multiple blades can be used on each arm to provide soft tissue retraction. The tongue on the clip fits into the longitudinal groove and is spring-loaded to lock the clip and blade in position on the arm. However, in prior art retractors the tongue and groove are generally the same shape with the tongue engaging the longitudinal groove to hold the blade in position. However, because the tongue is usually slightly smaller than the dimensions of the groove, the blades are not as firmly held as would be desired. The mounting clip of the present invention is improved to more securely clamp the longitudinal groove to prevent the blades from accidentally shifting position while a surgical procedure is being performed.

The improved clip has the spring-loaded clip mechanism and a tongue fitting the longitudinal groove. To prevent slipping the tongue is provided with a tapered surface that engages a sharp edge of the longitudinal groove to securely lock the position of a blade once placed in the incision.

The invention comprises a clip that fits into a clip socket on a blade mounting flange having a clip lever with a tongue that fits a substantial square cornered longitudinal groove in the retractor arms. The clip lever is mounted on the blade mounting flange by a pin and has a biasing spring beneath the lever to hold the tongue in the groove. The blade is mounted by pressing on a clip operating pad that locks the tongue in a raised position allowing the blade to be placed on the retractor arm. Release of the clip operating pad allows the tongue on the clip lever to drop into the longitudinal groove in the retractor arm. To overcome the flaw in previous clips the tongue is modified to hold the blade securely locked in the position holding tissue away from the surgical site when it is mounted on the retractor arm. To securely lock the blade on the arm the tongue is provided with a beveled edge that engages the sharp corner or edge of the longitudinal groove in the retractor arm.

In an alternate embodiment the tongue on the clip lever is thinner than the groove and has a beveled surface that engages the edge of the longitudinal groove. This arrangement tightly clamps the blade mounting flange and blade on the retractor arm preventing it from moving when in use.

The above and other novel features of the invention will be more fully understood from the following detailed description and the accompanying drawings, in which:

BRIEF DESCRIPTION OF THE DRAWINGS

FIG. 1 is an isometric view of blade locking mechanism for mounting a blade on a retractor arm according to the invention.

FIG. 2 is an exploded view of the improved blade locking mechanism according to the invention.

FIG. 3 is a sectional view taken at 3—3 of FIG. 1.

DETAILED DESCRIPTION OF THE INVENTION

Figure 4:
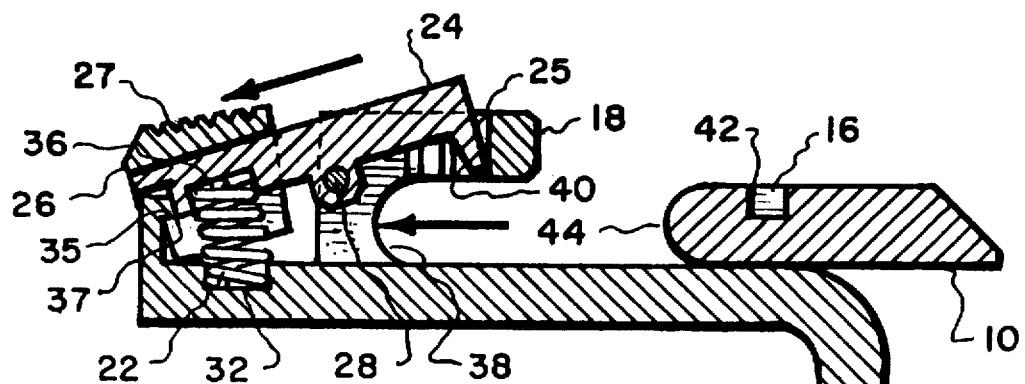
FIG. 4 is a sectional view similar to FIG. 3 illustrating the operation of the blade locking mechanism.

Surgical retractors are generally comprised of a cross arm having a pair of parallel arms forming a U-shaped frame with one of the arms being movable along the cross bar such as that shown in U.S. Pat. No. Design 361,381 referred to hereinabove. The movable arm is attached to the cross bar by a locking mechanism and includes a crank handle for precision adjustment of the movable arm relative to the stationary arm on the end of the cross bar.

A portion of one of the parallel arms 10 is illustrated in FIG. 1 having blade 12 attached. Several blades 12 in a variety of shapes and sizes can be attached to arm 10. Blade 12 is attached to arm 10 by a clip 14 that engages a longitudinal groove 16 in arm 10.

Clip 14 is mounted on mounting flange 18 of blade 12 as illustrated in FIG. 2. Blade mounting flange 18 has a recess 20 for receiving spring 22, clip lever 24 and clip operating pad 26. Spring 22, clip lever 24 and clip operating pad 26 are secured in socket or recess 20 by pin 28 passing through holes 30 in blade mounting flange 18. Spring 22 seats in socket 32 in clip mounting flange 34 with the other end seating in socket 36 in clip mounting lever 24. Retractor arm 10 fits into channel 38 formed between blade 12 and blade mounting flange 18 as will be described in greater detail hereinafter. Channel 38 is curved to fit the rear curved edge of blade 10.

A unique feature of the invention is illustrated in the cross sectional view of FIG. 3. Clip lever 24 has a tongue 25 that engages longitudinal groove 16 in arm 10 to securely hold blade 12 on the arm. In conventional practice tongue 25 is made to conform to the shape of longitudinal groove 16 but is slightly smaller. This however results in some "play" in the connection which can allow the blade to move during a surgical procedure. Any movement is unacceptable because it could cause interference and complicate the surgery. To securely lock blade 12 on arm 10 tongue 25 is provided with a tapered surface 40 constructed to engage sharp corner 42 of longitudinal groove 16. Channel 38 has a depth that causes tapered surface 40 to securely abut sharp edge 42 in channel 16 applying a "bite" to the connection to securely lock the clip in longitudinal groove 16 substantially preventing any movement of blade 12 during a surgical procedure.

The installation and removal of blade from the retractor frame arm 10 is shown in FIG. 4. To remove or mount blade 12 on arm 10 operating pad 26 is pressed by a thumb or finger applied to serrations 27 in the upper surface of operating pad 26 to provide a more secure operation. When pressed down operating pad 26 slides backward until lip 35 on flange 34 engages undercut shoulders 37 locking clip 14 in an "open" position. Pressure applied to operating pad 26 lifts forward end of the clip lever 24 retracting tongue 25 allowing rear edge 44 of blade 10 to be inserted or removed from channel 38. When rear curved edge 44 of blade 10 is securely seated in channel 38 and clip lever 24 released, beveled edge 40 on tongue 24 engages leading sharp edge 42 of longitudinal groove 16 securely locking blade on retractor arm 10. The sharp edge 42 of channel 16 "bites" into beveled surface 40 on tongue preventing blade from moving once it is secured to retractor arm 10.

Figure 5:
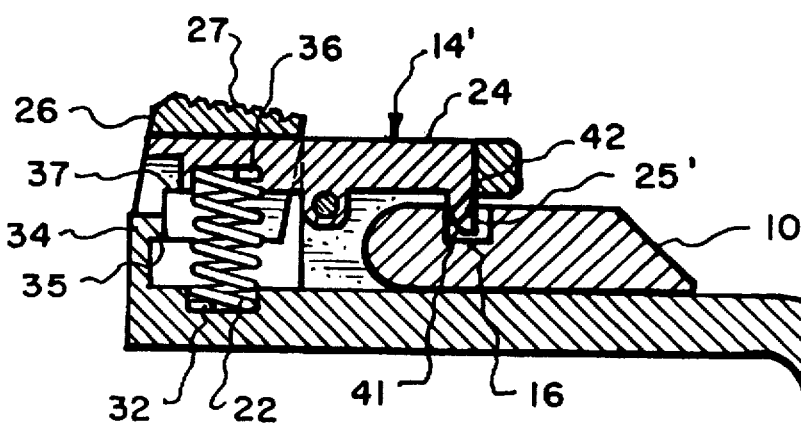
FIG. 5 is a sectional view similar to FIG. 3 illustrating an optional embodiment for locking a blade on a retractor arm.

An optional but less preferred embodiment is illustrated in FIG. 5. In this embodiment lever 24 is constructed with a narrower tongue 25'. Tongue 25' has a beveled surface 41 constructed to engage an edge 42 of longitudinal groove 16 of blade 10.

To mount or remove a retractor blade from arm 10 serrations 27 on operating pad 26 are pressed downward locking retracting tongue 25 (or 25' in embodiment in FIG. 5) in an open position allowing the arm to slide into channel 38 on blade mounting shoulder 18. Clip 14 is released by pushing operating pad 26 forward disengaging shoulders 37 from lip 35 allowing lever 24 to close with tongue 25 engaging longitudinal groove 16. In the first embodiment tapered surface 40 securely bites into and grips corner 42 of longitudinal 16. In the second embodiment beveled surface 41 on tongue 25' tightly engages corner 42 of longitudinal groove 16.

Thus there has been disclosed an improvement in surgical instrument retractors which substantially prevents movement of retractor blades once installed on retractor arm. In one embodiment the improvement comprises an improved clip having a tongue with a beveled edge to bite into and securely contact the corner of the longitudinal groove in the retractor arm. In a second embodiment the clip is manufactured with a tongue having a ridge that tightly fits the groove and engages the corner of the longitudinal groove.

This invention is not to be limited by the embodiment shown in the drawings and described in the description which is given by way of example and not of limitation, but only in accordance with the scope of the appended claims.

What is claimed is:

1. In a retractor comprised of a cross bar and a pair of parallel arms extending perpendicular from said cross bar the improvement comprising;

a longitudinal groove in each of said arms;

clip means for attaching retractor blades to said parallel arms, said clip means having a tongue for engaging said longitudinal groove in said respective parallel arm;

gripping means on said tongue for securely gripping an edge of said longitudinal groove to securely hold said blades on said arms.

2. The retractor according to claim 1 in which said gripping means comprises a tapered surface beneath said tongue adapted to engage and grip said edge of said longitudinal groove.

3. The retractor according to claim 1 in which said gripping means comprises said tongue having a beveled surface adapted to engage and grip said edge of said longitudinal groove.

* * * * *